(12) United States Patent
Sauter et al.

(10) Patent No.: US 6,977,001 B2
(45) Date of Patent: Dec. 20, 2005

(54) DYE COMPOSITIONS CONTAINING QUINOLINIUM SALTS

(75) Inventors: Guido Sauter, Thoerishaus (CH); Hans-Juergen Braun, Ueberstorf (CH); Nadia Duc-Reichlin, Forel (CH)

(73) Assignee: Wella AG, Darmstadt (DE)

( * ) Notice: Subject to any disclaimer, the term of this patent is extended or adjusted under 35 U.S.C. 154(b) by 98 days.

(21) Appl. No.: 10/361,380

(22) Filed: Feb. 10, 2003

(65) Prior Publication Data
US 2003/0177592 A1 Sep. 25, 2003

(30) Foreign Application Priority Data
Mar. 15, 2002 (DE) .......................... 102 11 413

(51) Int. Cl.$^7$ ................................................. A61K 7/13
(52) U.S. Cl. ........................ 8/423; 8/426; 8/654; 8/405
(58) Field of Search .......................... 8/405, 406, 409, 8/423, 426, 654

(56) References Cited

U.S. PATENT DOCUMENTS

| | | | |
|---|---|---|---|
| 3,149,105 A | | 9/1964 | Larive et al. |
| 3,945,837 A | * | 3/1976 | Miyata et al. ............ 106/31.43 |
| 6,371,993 B1 | * | 4/2002 | Moeller et al. ................. 8/407 |
| 6,485,529 B1 | * | 11/2002 | Javet et al. ..................... 8/405 |

FOREIGN PATENT DOCUMENTS

| | | | |
|---|---|---|---|
| DE | 43 35 623 A1 | | 4/1995 |
| DE | 197 45 292 A1 | | 4/1999 |
| DE | 199 50 404 A1 | | 5/2001 |
| GB | 1 102 891 | | 2/1968 |
| WO | 00/38633 | | 7/2000 |
| WO | WO 01/28507 | * | 4/2001 |

OTHER PUBLICATIONS

T.G. Deligeorgiev et al in Dyes and Pigments 41, 1999, pp. 49–54.
G . . . B Barlin et al in J. Chem Soc. Prekin Trans.2, 1975, pp. 298–302.
* cited by examiner Primary Examiner—Margaret Einsmann
(74) Attorney, Agent, or Firm—Michael J. Striker

(57) ABSTRACT

The dye composition (A) for dyeing fibers, especially keratin fibers, such as human hair, is made by mixing a first component (A1) and a second component (A2) and adding an alkalizing agent or an acidifying agent, as needed. The second component (A2) consists of at least one compound with a nucleophilic reaction center and the first component (A1) consists of at least one 1-alkyl quinolinium derivative of formula (Ia) or (Ib):

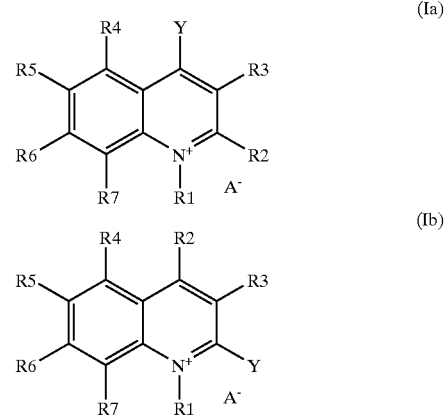

A multicomponent kit consisting of the first and second components packaged separately is also described as well as a method of dyeing fibers using the multicomponent kit.

15 Claims, No Drawings

DYE COMPOSITIONS CONTAINING QUINOLINIUM SALTS

BACKGROUND OF THE INVENTION

The subject matter of the present invention includes dye compositions, especially for keratin fibers, such as human hair, which contain 1-alkyl-quinolinium derivatives with nucleofuge groups at the 2 or the 4 position.

Direct dye compounds or oxidation dye compounds, which produce dye colors by reaction of certain developer substances with certain coupler substances in the presence of suitable oxidizing agents, have been used for dyeing fibers, such as hair, wool or fur. Intense dye colors with good fastness are indeed obtained with oxidation dyestuffs, but the oxidizing agents used to develop these colors can cause damage to the fibers in some cases. Furthermore some oxidation dyestuff products cause allergic reactions in suitably disposed persons. Direct dye compounds are applied under safe conditions, but have the disadvantage that their colors often have unsatisfactory fastness.

From DE-OS 43 35 623 it is known to use a combination of indolinone derivative compounds and compounds with primary or secondary amino groups, heterocyclic or aromatic hydroxy compounds for dyeing keratin fibers. DE-OS 197 45 292 teaches the use of a combination of certain malonaldehyde derivatives, such as malonaldehyde-bis-dialkylacetalene and amines or CH active compounds, for example 1-ethyl-2-methylquinolinium iodide or 1,2-dimethyl-quinolinium iodide, for dyeing hair without the use of an oxidizing agent. From WO 00/38633 the use of a combination of quinolinium aldehydes and amines, amino acids or oligopeptides or CH active compounds for dyeing hair with oxidizing agents is known. Furthermore the use of a combination of 1-alkyl-methylquinolinium salts, carbonyl compounds and alkanol amines for dyeing of hair without oxidizing agents is known from DE-OS 199 50 404.

The compositions and methods for dyeing fibers known from the art are however not satisfactory in every regard. There is a great need for dye compositions, which dye fibers with intense colors, but with good fastness, such as light fastness, wash fastness and friction fastness, under mild conditions, which means at maximum about 50° C.

SUMMARY OF THE INVENTION

It is an object of the present invention to provide a dyeing method and dye compositions, which permit safe and uniformly intense dyeing with good fastness, especially light fastness, wash fastness and friction fastness, under mild conditions without addition of oxidizing agents, especially hydrogen peroxide.

Surprisingly it has now been found that lasting or permanent dye colors with outstanding brilliance and color depth are safely obtained using a combination of (a) a 1-alkyl-quinolinium derivative compound of formula (Ia) or formula (Ib) substituted with a nucleofuge group in position 2 or position 4 with (b) a compound with a nucleophilic reaction center.

The subject matter of the present invention is thus a composition for dyeing fibers, for example cotton, jute, sisal, linen; or modified natural fibers, such as regenerated cellulose, nitrocellulose, alkyl cellulose, hydroxyalkyl cellulose or acetyl cellulose; or synthetic fibers, such as polyamide fibers, polyacryinitrile fibers, polyurethane fibers and polyester fibers; and especially keratin fibers, for example wool, silk or hair, particularly human hair. The composition for dyeing fibers according to the invention is obtained by mixing two components and adding an alkalizing agent or acidifying agent, if necessary. These two components are a second component A2, which comprises at least one compound with a nucleophilic reaction center, and a first component A1 comprising at least one 1-alkyl-quinolinium derivative of formula (Ia) or (Ib):

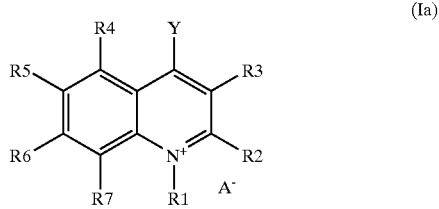

(Ia)

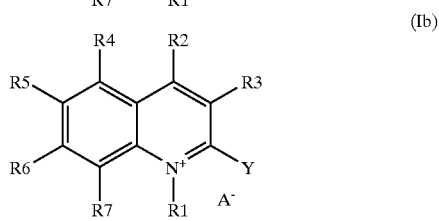

(Ib)

wherein R1 represents a straight chained or branched $C_1$- to $C_8$-alkyl group, a $C_1$- to $C_8$-monohydroxyalkyl group, a $C_2$- to $C_8$-polyhydroxyalkyl group or a $C_1$- to $C_8$-alkoxy-($C_1$- to $C_8$-)-alkyl group;

wherein R2, R3, R4, R5, R6 and R7 are the same or different, and, independently of each other, represent hydrogen, a straight chained or branched $C_1$- to $C_4$-alkyl group, a straight chained or branched $C_1$- to $C_4$-hydroxyalkyl group, a hydroxy group, a methoxy group, an ethoxy group, a benzyl group, a halogen (F, Cl, Br, I), a nitro group, a nitroso group, a cyano group, a trifluoromethyl group, a —COOH group, a —$CO_2R^a$ group, a —$CONHR^a$ group, a —$CON(R^a)_2$ group, a —$O(CO)R^a$, a —O—$SO_2CF_3$ group, a —$OCH_2$aryl group, a —$SO_2NH_2$ group, a —$SO_2CHF_2$ group, a —$SO_2CF_3$ group, a —$SO_2NH_2$ group, a —$SO_2NHR^a$ group, a —$SO_2N(R^a)_2$ group, a —$SO_2R^a$ group, a —$NH_2$ group, a —$NHR^a$ group, a —$N(R^a)_2$ group, a —$NHCOR^a$ group, a —$NHCOOR^a$ group, a —$CH_2NH_2$— group, a —$CH_2NHR^a$ group, a —$CH_2N(R^a)_2$ group or a —$PO(OR^a)_2$ group;

wherein $R^a$ represents a hydrogen atom, an optionally substituted aromatic carboxylic or heterocyclic group or a $C_1$- to $C_6$-alkyl group;

wherein Y represents an iodine atom, a bromine atom, a chlorine atom or an ethoxy group, a phenoxy group, a $CF_3$—$SO_2$—O group, an aryl-$SO_2$—O group or a (—$SO_3$)$^-$ group, the chlorine atom, the aryl-$SO_2$—O group and the (—$SO_3$)$^-$ group being particularly preferred; and wherein $A^-$ represents an anion of an organic or inorganic acid, preferably chloride, bromide, iodide, hydrogen sulfate, sulfate, toluene sulfonate, benzene sulfonate, monomethylsulfate, hexafluorophosphate, hexafluoroantimonate, tetrafluoroborate, tetraphenylborate, formate, acetate or propionate, wherein the chloride ion, the tetrafluoroborate ion, the acetate ion and the hydrogen sulfate ion are especially preferred.

The compounds of formula (Ia) and (Ib) are known in the literature or can be prepared by standard synthetic processes known in the literature, such as from U.S. Pat. No. 3,149,105 and GB Patent 1,102,891 or from T. G. Deligeorgiev, et al, in "Dyes and Pigments", 1999, pp. 49 to 54, and G. B. Barlin, in J. Chem. Soc. Perkin Trans. 2, 1975, pp. 298–302.

Suitable compounds of formula (Ia) and formula (Ib) include especially: 4-chloro-1-ethyl-quinolinium salt, 4,7-dichloro-1-ethyl-quinolinium salt, 4-chloro-1-ethyl-7-trifluoromethyl-quinolinium salt, 4-chloro-1-ethyl-6-nitroquinolinium salt, 4-chloro-1-methyl-quinolinium salt, 4-methoxy-1-methyl-quinolinium salt, 4-ethoxy-1-methyl-quinolinium salt, 4-ethoxy-1-ethyl-quinolinium salt, 4-iodo-1-methyl-quinolinium salt, 4-chloro-1-methyl-2-phenyl-quinolinium salt, 4-chloro-1-methyl-3-[(methylphenylamino)sulfonyl]quinolinium salt, 4-chloro-2-[[[4-(dimethylamino)phenyl]-imino]methyl]-6-methoxy-1-methyl-quinolinium salt, 4-chloro-1-ethyl-3-[(phenylamino)sulfonyl]-quinolinium salt, 4-chloro-6-dimethyl-carbamoyl-1-methyl-quinolinium salt, 4-chloro-1-ethyl-6-sulfamoyl-quinolinium salt, 4-chloro-1-ethyl-7-nitroquinolinium salt, 4-chloro-1-ethyl-7-methoxy-quinolinium salt, 2-chloro-1-methyl-quinolinium salt, 2,6-dichloro-1-methyl-quinolinium salt, 2-chloro-1-methyl-4-trifluoromethane-sulfonyloxy-quinolinium salt and 1-ethyl-4-(toluene-4-sulfonyloxy)-quinolinium salt. The 4-ethoxy-1-ethyl-quinolinium tetrafluoroborate, 4-chloro-1-ethyl-quinolinium tetrafluoroborate, 4,7-dichloro-1-ethyl-quinolinium tetrafluoroborate, 4-chloro-1-ethyl-7-trifluoromethyl-quinolinium tetrafluoroborate, 4-chloro-1-ethyl-6-nitroquinolinium tetrafluoroborate, 4-chloro-1-methylquinolinium chloride, 4-iodo-1-methyl-quinolinium iodide, 4-chloro-1-methyl-2-phenylquinolinium tetrafluoroborate, 4-chloro-1-methyl-3-[(methylphenylamino)sulfonyl]quinolinium methylsulfate, 4-chloro-2-[[[4-(dimethylamino)phenyl]imino]-methyl]-6-methoxy-1-methyl-quinolinium chloride, 4-chloro-1-ethyl-3-[(phenylamino)sulfonyl]quinolinium tetrafluoroborate, 4-chloro-6-dimethylcarbamoyl-1-methyl-quinolinium tetrafluoroborate, 4-chloro-1-ethyl-6-sulfamoyl-quinolinium tetrafluoroborate, 4-chloro-1-ethyl-6-formyl quinolinium tetrafluoroborate, 4-chloro-1-ethyl-7-nitro-quinolinium tetrafluoroborate, 4-chloro-1-ethyl-7-methoxy-quinolinium-tetrafluoroborate, 2-chloro-1-methyl-quinolinium tetrafluoroborate, 2,6-dichloro-1-methylquinolinium tetrafluoroborate, 1-ethyl-4-(toluene-4-sulfonyloxy)-quinolinium chloride, 1-ethyl-4-(toluene-4-sulfonyloxy)-quinolinium tetrafluoroborate, 1-ethyl-4-quinolinium sulfonate and 2-chloro-1-methyl-4-trifluoromethane sulfonyloxy quinolinium tetrafluoroborate are particularly preferred.

According to the present invention the term "compound with a nucleophilic reaction center" means a compound that can form nitrogen-carbon, oxygen-carbon or carbon-carbon bonds by substitution of the Y group from formula (Ia) or (Ib). A suitable compound with a nucleophilic reaction center thus contains, for example, a nitrogen atom or an oxygen atom or a negatively charged carbon atom (carban ion). For example, compounds with nucleophilic reaction centers that are suitable for the present invention are, for example, aliphatic or aromatic compounds with one or more amino groups, aliphatic or aromatic compounds with a hydrazine group, nitrogen-containing heterocyclic compounds, amino acids, oligopeptides with 2 to 9 amino groups, aromatic hydroxy compounds and CH-active compounds.

Suitable compounds with amino groups or hydrazine groups are, for example, 1,4-diaminobenzene (p-phenylenediamine), 1,4-diamino-2-methylbenzene sulfate, 1,4-diamino-2-(2-hydroxyethyl)benzene sulfate, 4-amino-2-(aminomethyl)-phenol dihydrochloride, 1,3-di(2,4-diamino-7-phenoxy)-propane tetrahydrochloride, 4-amino-1-naphthol hydrochloride 1,3-diamino-4-(2-hydroxyethoxy)-benzene sulfate, 5-amino-2-methylphenol, 5-((2-hydroxyethyl)-amino)-2-methoxyaniline sulfate, 1,4-diamino-2-methylbenzene sulfate, 1,4-diamino-2-(2-hydroxyethyl)benzene sulfate, 4-amino-2-(aminomethyl)-phenol dihydrochloride, 1,3-di(2,4-diaminophenoxy)-propane tetrahydrochloride, 4-amino-1-naphthol hydrochloride, 1,3-diamino-4-(2-hydroxyethoxy)benzene sulfate, 5-amino-2-methylphenol, 5-((2-hydroxyethyl) amino)-2-methoxyaniline sulfate, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-amino-methylbenzene, 1,4-diamino-2-hydroxymethylbenzene, 1,4-diamino-2-(2-hydroxyethoxy) benzene, 2-(2-(acetylamino)ethoxy)-1,4-diamino-benzene, 4-phenyl-aminoaniline, 4-dimethylaminoaniline, 4-diethylamino-aniline, 4-dipropylamino-aniline, 4-[ethyl (2-hydroxyethyl)amino]-aniline, 4-[di(2-hydroxy-ethyl) amino]-aniline, 4-[di(2-hydroxyethyl)amino]-2-methyl-aniline, 4-[(2-methoxy-ethyl)amino]-aniline, 4-[(3-hydroxypropyl)amino]-aniline, 4-[(2,3-dihydroxypropyl)-amino]-aniline, 1,4-diamino-2-(1-hydroxyethyl)benzene, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-aminophenyl) amino]butane, 1,8-bis-(2,5-diaminophenoxy)-3,6-dioxaoctane, 4-aminophenol, 4-amino-3-methyl-phenol, 4-amino-3-(hydroxymethyl)phenol, 4-amino-3-fluorophenol, 4-methyl-aminophenol, 4-amino-2-(aminomethyl)phenol, 4-amino-2-(hydroxymethyl)-phenol, 4-amino-2-fluorophenol, 4-amino-2-[(2-hydroxyethyl)-amino]methylphenol, 4-amino-2-methylphenol, 4-amino-2-(methoxymethyl)phenol, 4-amino-2-(2-hydroxyethyl) phenol, 2-aminophenol, 2-amino-6-methylphenol, 2-amino-5-methylphenol, 1,2,4-trihydroxybenzene, N-(3-dimethylaminophenyl)urea, 2-amino-4-[(2-hydroxyethyl) amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl) amino]-1,5-dimethoxybenzene, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene; 1-(2-amino-ethoxy)-2,4-diaminobenzene, 2-amino-1-(2-hydroxyethoxy)-4-methylamino-benzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methyl-ethyl)-phenol, 3-[(2-hydroxyethyl)amino]aniline, 3-[(2-aminoethyl)amino]aniline, 1,3-di(2,4-diaminophenoxy)propane, di(2,4-diaminophenoxy) methane, 1,3-diamino-2,4-dimethoxybenzene, 2,6-bis-(2-hydroxy-ethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichloro-phenol, 5-amino-2,4-dichlorophenol, 3-amino-2-methylphenol, 3-amino-6-chloro-6-methylphenol, 3-aminophenol, 2-[(3-hydroxyphenyl)amino]-acetamide, 5-[(2-hydroxyethyl) amino]-4-methoxy-2-methylphenol, 5-[(2-hydroxyethyl)

amino]-2-methylphenol, 3-[(2-hydroxyethyl)amino]phenol, 3-[(2-methoxyethyl)-amino]phenol, 5-amino-2-ethylphenol, 5-amino-2-methoxyphenol, 2-(4-amino-2-hydroxyphenoxy) ethanol, 5-[(3-hydroxypropyl)amino]-2-methylphenol, 3-[(2,3-dihydroxypropyl)amino]-2-methylphenol, 3-[(2-hydroxyethyl)-amino]-2-methylphenol, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylendioxy-phenol, 3,4-methylendioxyaniline, 5-[(2-hydroxyethyl)amino]-1,3-benzodioxol, 6-brom-1-hydroxy-3,4-methylendioxybenzene, 3,4-diaminobenzoic acid, 2-aminobenzoic acid, 3-aminobenzoic acid, 4-aminobenzoic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-amino-benzosulfonic acid, 3-aminobenzosulfonic acid, 4-aminobenzene-sulfonic acid, 3-amino-4-hydroxybenzene sulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalerie-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaminobenzene, 2,4,6-triaminoresorcinol, 4,5-diamino-1,2-benzenediol, 4,6-diaminopyrogallol, 3,5-diamino-4-hydroxy-1,2-benzenediol, aromatic anilines or phenols with one other aromatic group, such as 4,4'-diaminostilbene, 4,4'-diaminostilbene-2,2'-disulfononic acid monosodium salt or 4,4'-diaminostilbene-2,2'-disulfonic acid disodium salt, 4,4,-diamino-diphenylmethane, 4,4,-diaminodiphenylisulfide, 4,4,-diaminodiphenylsulfoxide, 4,4,-diaminodiphenylamine, 4,4,-diaminodiphenylamine-2-sulfonic acid, 4,4'-diaminobenzophenone, 4,4'-diaminobenzophenondiphenylether, 3,3',4,4-tetraaminodiphenyl, 3,3',4,4'-tetraaminobenzophenone, 1,3-bis-(2,4-diaminophenoxy)-propane, 1,8-bis-(2,5-diaminophenoxy)-3,6-dioxaoctane, 1,3-bis-(4-aminophenylamino)propane, 1,3-bis-(4-aminophenylamino)-2-propanol, 1,3-bis-[N-(4-aminophenyl)-2-hydroxy-ethylamino]-2-propanol, N,N-bis-[2-(4-aminophenoxy)-ethyl]-methylamine, phenylhydrazine, phenylhydrazine hydrochloride, 2,4-dinitro-1-hydrazinobenzene, 4-nitrophenylhydrazine, 2-nitrophenylhydrazine, 4-methoxyphenyl hydrazine, 4-methoxy-phenylhydrazine hydrochloride, p-tolylhydrazine, p-tolylhydrazine hydrochloride, 4-fluoro-phenylhydrazine, 4-fluoro-phenylhydrazine hydrochloride, 4-isopropyl-phenylhydrazine, 4-isopropyl-phenylhydrazine hydrochloride, 4-bromo-phenylhydrazine, 4-bromo-phenylhydrazine hydrochloride, o-tolylhydrazine hydrochloride, 2,3-dimethylphenyl-hydrazine hydrochloride hydrate, 2,4-dimethyl-phenylhydrazine hydrochloride, 2,5-dimethylphenylhydrazine hydrochloride, o-tolylhydrazine, 2,3-dimethylphenylhydrazine, 2,4-dimethylphenylhydrazine, 2,5-dimethylphenylhydrazine, 2,4,6-trichloro-phenylhydrazine, N-methyl-N-phenylhydrazine, N,N-diphenylhydrazine hydrochloride and N-phenyl-1,4-phenyendiamine.

Suitable nitrogen-containing heterocyclic compounds include, for example, 2-aminopyridine, 3-aminopyridine, 4-aminopyridine, 2-amino-3-hydroxy-pyridine, 2,6-diaminopyridine, 2,5-diaminopyridine, 2,3-diaminopyridine, 2-dimethylamino-5-aminopyridine, 2-methylamino-3-amino-6-methoxy-pyridine, 2,3-diamino-6-methoxypyridine, 2,6-dimethoxy-3,5-diaminopyridine, 2,4,5-triaminopyridine, 2,6-dihydroxy-3,4-dimethylpyridine, 3-amino-6-methoxy-2-(methylamino)-pyridine, 2,6-diamino-3,5-dimethoxypyridine, 3,5-diamino-2,6-dimethoxy-pyridine, 2,4-dihydroxy-5,6-diaminopyrimidine, 4,5,6-triamino-pyrimidine, 4-hydroxy-2,5,6-triamino-pyrimidine, 2-hydroxy-4,5,6-triamino-pyrimidine, 2,4,5,6-tetraamino-pyrimidine, 2,5,6-triamino-4-(1H)-pyrimidone, 2-methylamino-4,5,6-triamino-pyrimidine, 2,4-diaminopyrimidine, 4,5-diamino-pyrimidine, 2-amino-4-methoxy-6-methylpyrimidine, 2,6,8-trihydroxypurine, 4,5-diamino-1-(2-hydroxyethyl)-1H-pyrazole sulfate, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 3,5-diaminopyrazole, 3,5-diamino-1,2,4-triazole, 3-aminopyrazole, 3-amino-5-hydroxypyrazole, 2-aminoquinoline, 3,4-dihydro-6-hydroxy-1,4(2H)-benzoxazine, 6-amino-3,4-dihydro-1,4 (2H)-benzoxazine, 3-methyl-1-phenyl-5-pyrazoleone, 5,6-dihydroxyindole, 5,6-dihydroxyindoline, 5-hydroxyindole, 6-hydroxyindole, 7-hydroxyindole, 2,3-indolinedione, 3-aminoquinoline, 8-aminoquinoline, 4-aminomethylquinolin, 2-aminonicotinic acid, 6-aminonicotinic acid, 5-aminoisoquinoline, 5-amino-indazole, 6-aminoindazole, 5-aminobenzimidazole, 7-aminobenzimidazole, 7-aminobenzothiazole, 5-aminobenzothiazole, 2,5-dihydroxy-4-morpholinoaniline as well as indole and indoline derivatives, such as 4-aminoindole, 5-aminoindole, 6-aminoindole, 7-aminoindole, 5,6-dihydroxyindole, 5,6-dihydroxyindoline and 4-hydroxyindoline.

The above-named compounds can be used both in the free form and also in the form of their physiologically compatible salts, for example, as salts of inorganic acids, such as sulfuric or hydrochloric acid.

As amino acids both naturally occurring and also synthetic amino acids can be used in the compositions according to the invention. Especially the following amino acids can be included in the compounds of the invention: arginine, histidine, tyrosine, phenylalanine, dihydroxyphenylalanine, ornithine, lysine and tryptophane.

All naturally occurring oligopeptides or synthetic oligopeptides, as well as protein hydrolyzates or polypeptide hydrolyzates containing oligopeptides can be used in the compositions according to the invention, in so far as they have sufficient water solubility for use in the compositions according to the invention. The following exemplary compounds can be mentioned: glutathione or oligopepetides contained in the hydrolyzates of collagen, keratin, casein, elastin, soja protein, wheat broth or almond protein. The joint use of oligopeptides with compounds having primary or secondary amino groups or with aromatic hydroxy compounds is especially preferred.

Suitable aromatic compounds include, for example, 2-methylresorcinol, 4-methylresorcinol, 5-methylresorcinol, 2,5-dimethylresorcinol, resorcinol, 3-methoxyphenol, 1,2-benzendiol, hydroquinone, pyrogallol, phloroglucinol, hydroxyhydroquinone, 2-methoxyphenol, 3-methoxyphenol, 4-methoxyphenol, 3-dimethylaminophenol, 2-(2-hydroxyethyl)-phenol, 3,4-methylendioxyphenol, 2,4-dihydroxy-benzoic acid, 3,4-dihydroxybenzoic acid, 2,4-dihydroxyphenylacetic acid, 3,4-dihydroxyphenylacetic acid, gallic acid(3,4,5-trihydroxybenzoic acid), 2,4,6-trihydroxybenzoic acid, 2,4,6-trihydroxyacetophenone, 2-chlororesorcinol, 4-chlororesorcinol, 1-naphthol, 1,5-dihydroxynaphthalene, 2,3-dihydroxynaphthalene, 2,7-dihydroxynaphthalene, 4-hydroxy-2-naphthalene-sulfonic acid and 3,6-dihydroxy-2,7-naphthalene sulfonic acid.

Suitable CH-active compounds can include, for example: 1-ethyl-2-methylquinolinium iodide, 1-ethyl-2-methylquinolinium chloride, 1-ethyl-2-methylquinolinium tetrafluoroborate, 1-ethyl-2-methylquinolinium methylsulfate, 1-methyl-2-methylquinolinium iodide, 1-methyl-2-methylquinolinium chloride, 1-methyl-2-methylquinolinium tetrafluoroborate, 1-methyl-2-methylquinolinium methylsulfate, 1-ethyl-4-methylquinolinium iodide, 1-ethyl-4-methylquinolinium chloride, 1-ethyl-4-methylquinolinium tetrafluoroborate, 1-ethyl-4-methylquinolinium methylsulfate, 1-methyl-4-methylquinolinium iodide, 1-methyl-4-methylquinolinium chloride, 1-methyl-4-methylquinolinium tetrafluoroborate, 1-methyl-4-methylquinolinium methylsulfate, 1,2,3,3-tetramethyl-3H-indolium-hydrogen sulfate, 3-ethyl-1,2,3-trimethyl-3H-indolium perchlorate, 1,2,3,3,5-pentamethyl-3H-indolium iodide, 1,2,3,3,7-pentamethyl-3H-indolium tetrafluoroborate, 1,2,3,3,6,7-hexamethyl-3H-indolium-tetrafluoroborate, 1,2,3,3,5,7-hexamethyl-3H-indolium tetrafluoroborate, 1,2,3,3,4,7-hexamethyl-3H-indolium tetrafluoroborate, 5-fluoro-1,2,3,3-tetramethyl-3H-indolium iodide, 5-isopropyl-1,2,3,3-tetramethyl-3H-indolium iodide, 5-nitro-1,3,3-trimethyl-2-methylen-indoline, 5-methoxy-1,2,3,3-tetramethyl-3H-indolium iodide, 5-methoxy-6-nitro-1,2,3,3-tetramethyl-3H-indolium chloride, 5-hydroxy-1,2,3,3-tetramethyl-3H-indolium iodide, 5-N-acetylamino-1,2,3,3-tetramethyl-3H-indolium acetate, 2,3-dimethylbenzothiazolium iodide, 2,3-dimethylbenzothiazolium-p-toluene sulfonate, rhodanine, rhodanine-3-acetic acid, barbituric acid, thiobarbituric acid, 1,3-dimethylthiobarbituric acid, 1,3-diethylthiobarbituric acid, oxindole, 3-indoxyl acetate.

Prior to use the compounds of formula (Ia) and (Ib) are stored separately from the compounds with the nucleophilic reaction centers. The dye composition according to the invention usual comprises two components. These two components consist of a dye carrier (A1), which contains the compounds of formula (Ia) or (Ib), and, if necessary, direct dye compounds, and an additional dye carrier (A2), which contains the compound with the nucleophilic reaction center, and, if necessary, direct dye compounds. Both of these two components are mixed with each other immediately prior to application to form a ready-to-apply dye mixture (A) and then that is applied to the fibers to be dyed. Understandably it is also possible that one or both components (A1) and (A2) comprise individual components, which are mixed with each other prior to use. However a two-component kit consisting of component A1 and component A2 is especially preferred.

Although use of the above-described composition without addition of an oxidation agent is preferred on account of improved safety and care, use of the above-described dye composition in connection with an oxidizing agent is in principle possible. For example, when simultaneous bleaching of the fibers is desired or when the dye composition contains conventional oxidation dye pre-cursor compounds, an oxidizing agent may be added.

The compound of formula (Ia) or (Ib) or the compound with the nucleophilic reaction center is contained in its respective dye carrier (component (A1) or component (A2)) in a total amount of about 0.02 to 20 percent by weight, preferably from 0.2 to 10 percent by weight. Thus the compound of formula (Ia) or (Ib) or the compound with the nucleophilic reaction center are each contained in the ready-to-apply dye mixture (A) obtained by mixing the components (A1) and (A2) in a total amount of about 0.01 to 10 percent by weight, preferably from 0.1 to 5 percent by weight.

Furthermore the dye composition according to the invention can contain, as needed, additional conventional acidic or basic dye compounds, nitro dye compounds, azo dye compounds, quinone dye compounds and triphenylmethane dye compounds. The direct-dyeing dye compounds can be used in component (A1) and/or component (A2) in total amounts of about 0.02 to 20 percent by weight, preferably from 0.2 to 1 percent by weight. The total amount of the direct dye compounds in the ready-to-apply dye mixture (A) amounts to about 0.01 to 10 percent by weight, preferably from 0.1 to 5 percent by weight.

Preferably the composition according to the invention is free of aldehydes and ketones.

The preparation form of the ready-to-apply dye mixture (A), the component (A1) and/or the component (A2), for example, can be a solution, especially an aqueous or an aqueous-alcoholic solution. Additional suitable preparation forms are a cream, a gel, foam or an emulsion. These preparations contain a mixture of the compounds of formula (Ia) or (Ib) and the compounds with the nucleophilic reaction centers together with conventional cosmetic additives that are suitable for these preparations.

Conventional additives used in dye compositions in solutions, creams, emulsions, gels or foams include, for example, solvents, such as water, lower alcohols, for example, ethanol, n-propanol and isopropanol or glycols, such as glycerol and 1,2-propandiol; wetting agents or emulsifiers from the classes of anionic, cationic, amphoteric or nonionic surface-active substances, such as fatty alcohol sulfates, ethoxylated fatty alcohol sulfates, alkyl sulfonates, alkylbenzene sulfonates, alkyltrimethyl ammonium salts, alkyl betaines, ethoxylated fatty alcohols, ethoxylated nonyl phenols, fatty acid alkanol amides, ethoxylated fatty acid esters; thickeners, such as higher fatty alcohols, starches or cellulose derivatives, perfumes, hair pre-treatment agents, conditioners, hair swelling agents, preservatives, petrolatum (Vaseline®), paraffin oils and fatty acids, as well as additional care materials, such as cationic resins, lanolin derivatives, cholesterol, pantothenic acid and betaine. The above-mentioned ingredients are employed in amounts that are conventional for their purposes. For example the wetting agents and emulsifiers are used in concentrations of about 0.5 to 30 percent by weight (in relation to the total dye carrier mass). The thickeners, are used in an amount of about 0.1 to 30 percent by weight (in relation to the total dye carrier mass) and the care materials, in a concentration of about 0.1 to 5 percent by weight (in relation to the total dye carrier mass).

The pH of the ready-to-apply dye composition amounts usually to about 3 to 11, preferably about 5 to 11. A pH of from 7 to 10 is particularly preferred. The pH of the ready-to-apply dye composition (A) results when the component (A1) containing the compound of formula (Ia) or (Ib) is mixed with the component (A2) containing the compound with the nucleophilic reaction center. The resulting pH depends on the pH of components (A1) and (A2) as well as the mixture ratio of the components. However the pH of the ready-to-apply dye mixture (A) can be adjusted by addition of a suitable alkalizing agent or an acid to obtain the desired value after mixing of components (A1) and (A2).

Alkalizing agents that are suitable for adjusting the pH of the ready-to-apply dye mixture (A) and the components (A1) or (A2) include, for example, alkanolamines, alkylamines, alkali hydroxides or ammonium hydroxides, alkali carbonates or ammonium carbonates and ammonia solution or acids, such as lactic acid, acetic acid, tartaric acid, phosphoric acid, hydrochloric acid, citric acid, ascorbic acid and boric acid.

The ready-to-apply dye mixture (A) is prepared immediately prior to application by mixing the component (A1) containing the compounds of formula (Ia) or (Ib) with the component (A2) containing the compound with the nucleophilic reaction center (if necessary with addition of an alkalizing agent or an acid). Then the ready-to-apply dye mixture (A) is applied to the fibers and allowed to remain and act on the fibers for 5 to 60 minutes, preferably from 15 to 30 minutes, at a temperature of from 20 to 50° C., especially at 30 to 40° C. Subsequently the fibers are rinsed with water and washed as needed with a shampoo.

The dye composition according to the invention provides a broad palette of color shades from yellow-red to blue and brown-black of outstanding fastness. A safe, uniform and lasting dyeing of the fibers, especially keratin fibers, for example human hair, is obtained, without addition of oxidizing agents.

The following examples should illustrate the subject matter of the invention in more detailed without limiting the claims appended below.

EXAMPLES

Examples 1 to 7

Hair Dye Composition

| Component (A1): | |
| --- | --- |
| Compound of formula (Ia) or (Ib) | Amount according to Table I |
| Decylglucoside | 4.0 g |
| Ethylenediamine tetraacetate disodium salt | 0.2 g |
| Ethanol | 5.0 g |
| Water, desalinated | to 100.0 g |

| Component (A2): | |
| --- | --- |
| Compound with nucleophilic reaction center | Amount according to Table I |
| Decylglucoside | 4.0 g |
| Ethylenediamine tetraacetate disodium salt | 0.2 g |
| Ethanol | 5.0 g |
| 25% aqueous ammonia solution | 6.0 g |
| Water, desalinated | to 100.0 g |

The component (A1) and the component (A2) are mixed with each other in a ratio of 1:1. The ready-to-apply hair dye mixture (A) is applied to the hair and is distributed uniformly with a brush. After an acting time of 30 minutes at 40° C. the hair is washed with a shampoo, subsequently rinsed with lukewarm water and then dried.

The amounts used and the dyed hair colors produced are tabulated in Table I.

Examples 8 to 14

Hair Dye Composition

| Component (A1): | |
| --- | --- |
| Compound of formula (Ia) or (Ib) | Amount according to Table II |
| Cocoamidopropylbetaine | 7.5 g |
| Ethanol | 5.0 g |
| Water, desalinated | to 100.0 g |

| Component (A2): | |
| --- | --- |
| Compound with nucleophilic reaction center | Amount according to Table II |
| Cocoamidopropylbetaine | 7.5 g |
| Ethanol | 5.0 g |
| 25% aqueous ammonia solution | 6.0 g |
| Water, desalinated | to 100.0 g |

The component (A1) and the component (A2) are mixed with each other in a ratio of 1:1. The ready-to-apply hair dye mixture (A) is applied to the hair and is distributed uniformly with a brush. After an acting time of 30 minutes at 40° C. the hair is washed with a shampoo, subsequently rinsed with lukewarm water and then dried.

The amounts used and the dyed hair colors produced are tabulated in Table II.

Examples 15 to 24

Hair Dye Composition

| Component (A1): | |
| --- | --- |
| Compound of formula (Ia) or (Ib) | Amount according to Table III |
| Cetylstearyl alcohol | 12.0 g |
| Polyethylene glycol octadecyl ether (Brij ® 78P of Fluka) | 2.5 g |
| Water, desalinated | to 100.0 g |

| Component (A2): | |
| --- | --- |
| Compound with nucleophilic reaction center | Amount according to Tables I-III |
| Cetylstearyl alcohol | 12.0 g |
| Polyethylene glycol octadecyl ether (Brij ® 78P of Fluka) | 2.5 g |
| Water, desalinated | to 100.0 g |

The cetyl stearyl alcohol is melted at 80° C. to make the components (A1) and (A2). The polyethylene glycol octadecyl ether is heated with 95% of the water and added to the melted cetyl stearyl alcohol. A cream results from this procedure. The compound with the nucleophilic reaction center or the compound of formula (Ia) or (Ib) is subsequently added with the remaining water at room temperature.

Then component (A1) and the component (A2) are mixed with each other in a ratio of 1:1. The pH of the resulting mixture is adjusted by addition of a 25% aqueous ammonia solution to the pH value reported in Table III. The ready-to-apply hair dye mixture (A) is applied to the hair and is distributed uniformly with a brush. After an acting time of 30 minutes at 40° C. the hair is washed with a shampoo, subsequently rinsed with lukewarm water and then dried.

The amounts used and the dyed hair colors produced are tabulated in Table III.

The L*a*b* color values reported for the present examples were measured with a calorimeter from Minolta Co., namely the Minolta Chromameter Type II. The "L" stands for the lightness or brightness (the less the L value, the more the color intensity), while "a" is a measure of the portion of red in the color (the more the a value, the greater the proportion of red). The "b" is a measure of the blue color. The greater the proportion of blue, the more negative is the b value.

All percentages in this application, unless otherwise indicated, are percentages by weight.

TABLE I

HAIR DYE COMPOSITION INGREDIENTS, AMOUNTS AND RESULTING HAIR COLORS

| Ex. No. | Component (A1)/ Component (A2) | Color Shade | Measured Color Values L | a | b |
|---|---|---|---|---|---|
| 1 | (A1) 4-chloro-1-ethyl-quinolinium tetrafluoroborate, 0.70 g (A2) 1,4-diaminobenzene, 0.27 g | Yellow | 77.00 | −1.12 | +67.37 |
| 2 | (A1) 4-chloro-1-ethyl-quinolinium tetrafluoroborate, 0.70 g (A2) 1,4-diamino-2-methylbenzene sulfate, 0.55 g | Yellow | 67.61 | +0.28 | +54.88 |
| 3 | (A1) 4-chloro-1-ethyl-quinolinium tetrafluoroborate, 0.70 g (A2) 1,4-diamino-2-(2-hydroxyethyl)-benzene sulfate, 0.63 g | Yellow | 71.23 | +0.02 | +61.12 |
| 4 | (A1) 4-chloro-1-ethyl-quinolinium tetrafluoroborate, 0.70 g (A2) 4,5-diamino-1-(2-hydroxyethyl)-1H-pyrazole sulfate, 0.60 g | Yellow | 76.13 | +2.24 | +34.69 |
| 5 | (A1) 4-chloro-1-ethyl-quinolinium tetrafluoroborate, 0.70 g (A2) 4-amino-2-(aminomethyl)-phenol dihydrochloride, 0.53 g | Yellow | 60.71 | +3.10 | +26.46 |
| 6 | (A1) 4-chloro-1-ethyl-quinolinium tetrafluoroborate, 0.70 g (A2) 1,3-di(2,4-diaminophenoxy)-propane tetrahydrochloride, 1.09 g | Yellow | 69.04 | −1.32 | +40.76 |
| 7 | (A1) 4-chloro-1-ethyl-quinolinium tetrafluoroborate, 0.70 g (A2) 4-amino-1-naphthol hydrochloride, 0.49 g | brown | 52.01 | +7.87 | +21.33 |

TABLE II

HAIR DYE COMPOSITION INGREDIENTS, AMOUNT AND RESULTING HAIR COLORS

| Ex. No. | Component (A1)/ Component (A2) | Color Shade | Measured Color Values L | a | b |
|---|---|---|---|---|---|
| 8 | (A1) 4-chloro-1-ethyl-quinolinium tetrafluoroborate, 0.70 g (A2) 1,4-diaminobenzene, 0.27 g | Yellow | 73.05 | −0.97 | +61.18 |
| 9 | (A1) 4-chloro-1-ethyl-quinolinium tetrafluoroborate, 0.70 g (A2) 1,4-diamino-2-methylbenzene sulfate, 0.55 g | Yellow | 70.54 | +1.86 | +61.19 |
| 10 | (A1) 4-chloro-1-ethyl-quinolinium tetrafluoroborate, 0.70 g (A2) 1,4-diamino-2-(2-hydroxyethyl)-benzene sulfate, 0.63 g | Yellow | 72.97 | −0.45 | +61.60 |
| 11 | (A1) 4-chloro-1-ethyl-quinolinium tetrafluoroborate, 0.70 g (A2) 4,5-diamino-1-(2-hydroxyethyl)-1H-pyrazole sulfate, 0.60 g | Yellow | 73.11 | +6.03 | +28.58 |
| 12 | (A1) 4-chloro-1-ethyl-quinolinium tetrafluoroborate, 0.70 g (A2) 4-amino-2-(aminomethyl)-phenol dihydrochloride, 0.53 g | Yellow | 63.02 | +2.81 | +27.44 |
| 13 | (A1) 4-chloro-1-ethyl-quinolinium tetrafluoroborate, 0.70 g (A2) 1,3-di(2,4-diaminophenoxy)-propane tetrahydrochloride, 1.09 g | Yellow | 68.16 | −1.10 | +32.82 |
| 14 | (A1) 4-chloro-1-ethyl-quinolinium tetrafluoroborate, 0.70 g (A2) 4-amino-1-naphthol hydroxychloride, 0.49 g | brown | 56.60 | +8.49 | +24.73 |

TABLE III

HAIR DYE COMPOSITION INGREDIENTS, AMOUNTS AND RESULTING HAIR COLORS

| Ex. No. | Component (A1)/ Component (A2) | Color Shade | Measured Color Values L | a | b |
|---|---|---|---|---|---|
| 15 | (1) 4,7-dichloro-1-ethyl-quinolinium tetrafluoroborate, 0.78 g (A2) 1,3-diamino-4-(2-hydroxyethyl)-benzene sulfate, 0.67 g; $pH_m = 10.0$ | Yellow | 80.78 | −3.37 | +60.74 |
| 16 | (A1) 4,7-dichloro-1-ethyl-quinolinium tetrafluoroborate, 0.78 g (A2) 1,4-diamino-2-methylbenzene sulfate, 0.55 g; $pH_m = 10.0$ | Yellow | 73.93 | +8.79 | +73.69 |
| 17 | (A1) 4-chloro-1-ethyl-quinolinium tetrafluoroborate, 0.70 g (A2) 5-amino-2-methylphenol, 0.31 g; $pH_m = 10.5$ | Yellow | 77.67 | +0.82 | +30.07 |
| 18 | (A1) 4-chloro-1-ethyl-quinolinium tetrafluoroborate, 0.70 g (A2) 5-((2-hydroxyethyl)-amino)-2-methoxy aniline sulfate (1:1)-hydrate (1:1); 0.75 g; $pH_m = 11$ | brown | 53.89 | +5.06 | +12.89 |

TABLE III-continued

HAIR DYE COMPOSITION INGREDIENTS, AMOUNTS AND RESULTING HAIR COLORS

| Ex. No. | Component (A1)/ Component (A2) | Color Shade | Measured Color Values | | |
|---|---|---|---|---|---|
| | | | L | a | b |
| 19 | (A1) 4-chloro-1-ethyl-quinolinium tetrafluoroborate, 0.70 g (A2) 2,6,8-trihydroxypurine, 0.42 g, $pH_m$ = 11 | Rose | 57.75 | +30.42 | −3.83 |
| 20 | (A1) 4,7-dichloro-1-ethyl-quinolinium tetrafluoroborate, 0.79 g (A2) 1,4-diamino-2-methyl-benzene sulfate, 0.55 g | Yellow-Orange | 73.94 | +8.79 | +73.69 |
| 21 | (A1) 4,7-dichloro-1-ethyl-quinolinium tetrafluoroborate, 0.79 g (A2) 2-(2,4-diaminophenoxy)-ethanol, 0.40 g | Bright Yellow | 80.78 | −3.37 | +60.74 |
| 22 | (A1) 4-chloro-1-ethyl-quinolinium tetrafluoroborate, 0.70 g (A2) 1-ethyl-4-methyl-quinolinium tetrafluoroborate, 0.65 g | Royal Blue | 42.03 | +17.75 | −45.36 |
| 23 | (A1) 4,7-dichloro-1-ethyl-quinolinium tetrafluoroborate, 0.78 g (A2) 1-ethyl-4-methyl-quinolinium tetrafluoroborate, 0.65 g | Royal Blue | 41.96 | +18.11 | −46.30 |
| 24 | (A1) 4,7-dichloro-1-ethyl-quinolinium tetrafluoroborate, 0.78 g (A2) 1-ethyl-2-methyl-quinolinium iodide, 0.75 g | Pink | 45.47 | +54.39 | −26.87 |

The disclosure in German Patent Application 102 11 413.7 of Mar. 15, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in dye compositions containing quinolinium salts, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An aqueous or aqueous alcoholic dye composition (A) for dyeing fibers made by mixing a first component (A1) and a second component (A2) to form a dye mixture and adding an alkalizing agent or an acidifying agent to the dye mixture, as needed for adjustment of pH to a value between 3 and 11, wherein said second component (A2) comprises at least one compound with a nucleophilic reaction center and said first component (A1) comprises at least one 1-alkyl quinolinium derivative of formula (Ia) or (Ib):

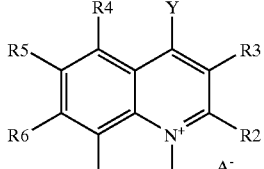

(Ia)

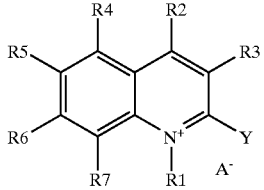

(Ib)

wherein R1 represents a straight chained or branched $C_1$- to $C_8$-alkyl group, a $C_1$- to $C_8$-monohydroxyalkyl group, a $C_2$- to $C_8$-polyhydroxyalkyl group or a $C_1$- to $C_8$-alkoxy-($C_1$- to $C_8$-)-alkyl group;

wherein R2, R3, R4, R5, R6 and R7 are the same or different, and, independently of each other, represent hydrogen, a straight changed or branched $C_1$- to $C_4$-alkyl group, a straight changed or branched $C_1$- to $C_4$-hydroxyalkyl group, a hydroxy group, a methoxy group, an ethoxy group, a benzyl group, a halogen, a nitro group, a nitroso group, a cyano group, a trifluoromethyl group, a —COOH group, a —$CO_2R^a$ group, a —$CONHR^a$ group, a —$CON(R^a)_2$ group, a —O(CO)$R^a$, a —O—$SO_2CF_3$ group, a —$OCH_2$aryl group, a —$SO_2NH_2$ group, a —$SO_2CHF_2$ group, a —$SO_2CF_3$ group, a —$SO_2NH_2$ group, a —$SO_2NHR^a$ group, a —$SO_2N(R^a)_2$ group, a —$SO_2R^a$ group, a —$NH_2$ group, a —$NHR^a$ group, a —$N(R^a)_2$ group, a —$NHCOR^a$ group, a —$NHCOOR^a$ group, a —$CH_2NH_2$ group, a —$CH_2NHR^a$ group, a —$CH_2N(R^a)_2$ group or a —$PO(OR^a)_2$ group;

wherein $R^a$ represents a hydrogen atom, an optionally substituted aromatic carboxylic or heterocyclic group or a $C_1$- to $C_6$-alkyl group;

wherein Y represents an iodine atom, a bromine atom, a chlorine atom or an ethoxy group, a phenoxy group, a $CF_3$—$SO_2$—O group, an aryl-$SO_2$—O group or a (—$SO_3$)$^-$ group;

wherein $A^-$ represents an anion of an organic or inorganic acid; and wherein said at least one compound with said nucleophilic reaction center is selected from the group consisting of aliphatic compounds with at least one amino group, aromatic compounds with at least one amino group, aliphatic compounds with at least one hydrazine group, aromatic compounds with a hydrazine group, nitrogen-containing heterocyclic compounds, amino acids, oligopeptides with 2 to 9 amino acid groups, aromatic hydroxy compounds and CH-active compounds.

2. The dye composition as defined in claim 1, wherein said at least one 1-alkyl-quinolinium derivative of formula (Ia) or (Ib) is selected from the group consisting of 4-chloro-1-ethyl-quinolinium salt, 4,7-dichloro-1-ethyl-quinolinium salt, 4-chloro-1-ethyl-7-trifluoromethyl-quinolinium salt, 4-chloro-1-ethyl-6-nitroquinolinium salt, 4-chloro-1-methyl-quinolinium salt, 4-methoxy-1-methyl-quinolinium salt, 4-ethoxy-1-methyl-quinolinium salt, 4-ethoxy-1-ethyl-quinolinium salt, 4-iodo-1-methyl-quinolinium salt, 4-chloro-1-methyl-2-phenyl-quinolinium salt, 4-chloro-1-methyl-3-[(methylphenylamino)sulfonyl]quinolinium salt, 4-chloro-2-[[[4-(di-methylamino)phenyl]-imino[methyl]-6-methoxy-1-methyl-quinolinium salt, 4-chloro-1-ethyl-3-[(phenylamino)sulfonyl]-quinolinium salt, 4-chloro-6-dimethyl-carbamoyl-1-methyl-quinolinium salt, 4-chloro-1-ethyl-6-sulfamoyl-quinolinium salt, 4-chloro-1-ethyl-7-nitroquinolinium salt, 4-chloro-1-ethyl-7-methoxy-quinolinium salt, 2-chloro-1-methyl-quinolinium salt, 2,6-dichloro-1-methyl-quinolinium salt, 2-chloro-1-methyl-4-trifluoromethane-sulfonyloxy-quinolinium salt and 1-ethyl-4-(toluene-4-sulfonyloxy)-quinolinium salt.

3. The dye composition as defined in claim 1, wherein said at least one 1-alkyl-quinolinium derivative of formula (Ia) or (Ib) is selected from the group consisting of 4-ethoxy-1-ethyl-quinolinium tetrafluoroborate, 4-chloro-1-ethyl-quinolinium tetrafluoroborate, 4,7-dichloro-1-ethyl-quinolinium tetrafluoroborate, 4-chloro-1-ethyl-7-trifluoromethyl-quinolinium tetrafluoroborate, 4-chloro-1-ethyl-6-nitroquinolinium tetrafluoroborate, 4-chloro-1-methylquinolinium chloride, 4-iodo-1-methyl-quinolinium iodide, 4-chloro-1-methyl-2-phenylquinolinium tetrafluoroborate, 4-chloro-1-methyl-3-[(methylphenylamino)-sulfonyl]quinolinium methylsulfate, 4-chloro-2-[[[4-(dimethylamino)phenyl]imino]methyl]-6-methoxy-1-methyl-quinolinium chloride, 4-chloro-1-ethyl-3-[(phenylamino)sulfonyl]quinolinium tetrafluoroborate, 4-chloro-6-dimethylcarbamoyl-1-methyl-quinolinium tetrafluoroborate, 4-chloro-1-ethyl-6-sulfamoyl-quinolinium tetrafluoroborate, 4-chloro-1-ethyl-6-formyl quinolinium tetrafluoroborate, 4-chloro-1-ethyl-7-nitro-quinolinium tetrafluoroborate, 4-chloro-1-ethyl-7-methoxy-quinolinium-tetrafluoroborate, 2-chloro-1-methyl-quinolinium tetrafluoroborate, 2,6-dichloro-1-methylquinolinium tetrafluoroborate, 1-ethyl-4-(toluene-4-sulfonyloxy)-quinolinium chloride, 1-ethyl-4-(toluene-4-sulfonyloxy)-quinolinium tetrafluoroborate, 1-ethyl-4-quinolinium sulfonate and 2-chloro-1-methyl-4-trifluoromethane sulfonyloxy quinolinium tetrafluoroborate.

4. The dye composition as defined in claim 1, wherein said value of said pH from is 5 to 11.

5. The dye composition as defined in claim 1, wherein said at least one 1-alkyl-quinolinium derivative of formula (Ia) or (Ib) is present in a total amount of from 0.02 to 20 percent by weight in said first component (A1) and said at least one compound with said nucleophilic reaction center is present in said second component (A2) in a total amount of from 0.02 to 20 percent by weight.

6. The dye composition as defined in claim 1, wherein said at least one 1-alkyl-quinolinium derivative of formula (Ia) or (Ib) and said at least one compound with said nucleophilic reaction center are each present in a total amount of 0.01 to 10 percent by weight.

7. The dye composition as defined in claim 1, in the form of a solution, an emulsion, foam, a cream or a gel.

8. The dye composition as defined in claim 1, wherein said first component is present in the form of a solution, an emulsion, foam, a cream or a gel.

9. The dye composition as defined in claim 1, wherein said second component is present in the form of a solution, an emulsion, foam, a cream or a gel.

10. The dye composition as defined in claim 1, wherein at least one of said first component and said second component includes at least one direct dye compound and said at least one direct dye compound is selected from the group consisting of acidic dye compounds, basic dye compounds, nitro dye compounds, azo dye compounds, quinone dye compounds and triphenyl-methane dye compounds.

11. The dye composition as defined in claim 1, wherein at least one of said first component (A1) and said second component (A2) consist or consists of a plurality of separate components.

12. A multi-component kit, comprising a first component (A1) containing at least one 1-alkylquinolinium compound of formula (Ia) or (Ib) and a second component (A2) containing at least one compound with a nucleophilic reaction center;

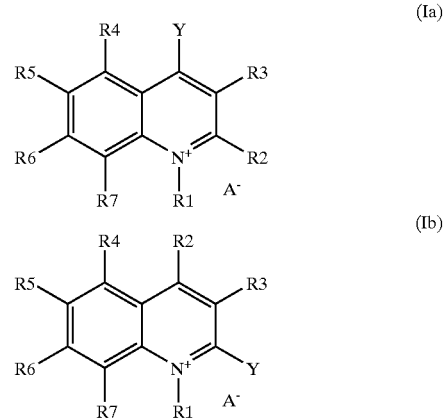

wherein R1 represents a straight chained or branched $C_1$- to $C_8$-alkyl group, a $C_1$- to $C_8$-monohydroxyalkyl group, a $C_2$- to $C_8$-polyhydroxyalkyl group or a $C_1$- to $C_8$-alkoxy-($C_1$- to $C_8$-)-alkyl group;

wherein R2, R3, R4, R5, R6 and R7 are the same or different, and, independently of each other, represent hydrogen, a straight changed or branched $C_1$- to $C_4$-alkyl group, a straight changed or branched $C_1$- to $C_4$-hydroxyalkyl group, a hydroxy group, a methoxy group, an ethoxy group, a benzyl group, a halogen, a nitro group, a nitroso group, a cyano group, a trifluoromethyl group, a —COOH group, a —CO$_2$R$^a$ group, a —CONHR$^a$ group, a —CON(R$^a$)$_2$ group, a —O(CO)R$^a$, a —O—SO$_2$CF$_3$ group, a —OCH$_2$aryl group, a —SO$_2$NH$_2$ group, a —SO$_2$CHF$_2$ group, a —SO$_2$CF$_3$ group, a —SO$_2$NH$_2$ group, a —SO$_2$NHR$^a$ group, a —SO$_2$N(R$^a$)$_2$ group, a —SO$_2$R$^a$ group, a —NH$_2$ group, a —NHR$^a$ group, a —N(R$^a$)$_2$ group, a —NHCOR$^a$ group, a —NHCOOR$^a$ group, a —CH$_2$NH$_2$ group, a —CH$_2$NHR$^a$ group, a —CH$_2$N(R$^a$)$_2$ group or a —PO(OR$^a$)$_2$ group;

wherein R$^a$ represents a hydrogen atom, an optionally substituted aromatic carboxylic or heterocyclic group or a $C_1$- to $C_6$-alkyl group;

wherein Y represents an iodine atom, a bromine atom, a chlorine atom or an ethoxy group, a phenoxy group, a CF$_3$—SO$_2$—O group, an aryl-SO$_2$—O group or a (—SO$_3$)$^-$ group;

wherein A$^-$ represents an anion of an organic or inorganic acid; and wherein said at least one compound with said nucleophilic reaction center is selected from the group consisting of aliphatic compounds with at least one amino group, aromatic compounds with at least one amino group, aliphatic compounds with at least one hydrazine group, aromatic compounds with a hydrazine group, nitrogen-containing heterocyclic compounds, amino acids, oligopeptides with 2 to 9 amino acid groups, aromatic hydroxy compounds and CH-active compounds.

13. The multi-component kit as defined in claim 12, further comprising a third component containing an alkalizing agent or an acidifying agent in an amount necessary to adjust a pH of a dye mixture formed by mixing the first component (A1) with the second component (A2) to a value between 3 and 11.

14. A method of dyeing fibers, said method comprising the steps of:
   a) immediately prior to application to the fibers, mixing a first component (A1) containing at least one dye compound with a second component (A2) containing at least one compound with a nucleophilic reaction center to form an aqueous or aqueous alcoholic ready-to-apply dye mixture (A) and adding an alkalizing agent or an acidifying agent to the aqueous or aqueous alcoholic dye mixture (A), as needed, for adjustment of pH of the dye mixture (A) to a value between 3 and 11;
   b) applying aqueous or aqueous alcoholic ready-to-apply dye mixture (A) having said value of said pH to the fibers in an amount sufficient for the dyeing of the fibers;
   c) allowing the ready-to-apply dye mixture to act on the fibers for a time interval of from 5 to 60 minutes at a temperature of from 20 to 50° C.; and
   d) subsequently washing the fibers with a shampoo, as needed, rinsing with water and then drying the fibers;
   wherein said at least one dye compound consists of at least one 1-alkylquinolinium compound of formula (Ia) or (Ib):

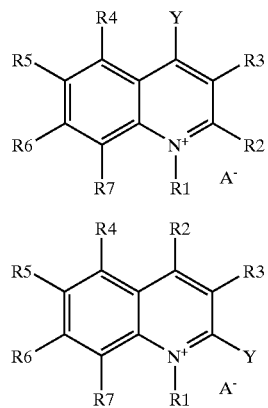

wherein R1 represents a straight chained or branched $C_1$- to $C_8$-alkyl group, a $C_1$- to $C_8$-monohydroxyalkyl group, a $C_2$- to $C_8$-polyhydroxyalkyl group or a $C_1$- to $C_8$-alkoxy-($C_1$- to $C_8$-)-alkyl group;

wherein R2, R3, R4, R5, R6 and R7 are the same or different, and, independently of each other, represent hydrogen, a straight changed or branched $C_1$- to $C_4$-alkyl group, a straight changed or branched $C_1$- to $C_4$-hydroxyalkyl group, a hydroxy group, a methoxy group, an ethoxy group, a benzyl group, a halogen, a nitro group, a nitroso group, a cyano group, a trifluoromethyl group, a —COOH group, a —$CO_2R^a$ group, a —$CONHR^a$ group, a —$CON(R^a)_2$ group, a —O(CO)$R^a$, a —O—$SO_2CF_3$ group, a —$OCH_2$aryl group, a —$SO_2NH_2$ group, a —$SO_2CHF_2$ group, a —$SO_2CF_3$ group, a —$SO_2NH_2$ group, a —$SO_2NHR^a$ group, a —$SO_2N(R^a)_2$ group, a —$SO_2R^a$ group, a —$NH_2$ group, a —$NHR^a$ group, a —$N(R^a)_2$ group, a —$NHCOR^a$ group, a —$NHCOOR^a$ group, a —$CH_2NH_2$ group, a —$CH_2NHR^a$ group, a —$CH_2N(R^a)_2$ group or a —$PO(OR^a)_2$ group;

wherein $R^a$ represents a hydrogen atom, an optionally substituted aromatic carboxylic or heterocyclic group or a $C_1$- to $C_6$-alkyl group;

wherein Y represents an iodine atom, a bromine atom, a chlorine atom or an ethoxy group, a phenoxy group, a $CF_3$—$SO_2$—O group, an aryl-$SO_2$—O group or a (—$SO_3$)$^-$ group;

wherein $A^-$ represents an anion of an organic or inorganic acid; and wherein said at least one compound with said nucleophilic reaction center is selected from the group consisting of aliphatic compounds with at least one amino group, aromatic compounds with at least one amino group, aliphatic compounds with at least one hydrazine group, aromatic compounds with a hydrazine group, nitrogen-containing heterocyclic compounds, amino acids, oligopeptides with 2 to 9 amino acid groups, aromatic hydroxy compounds and CH-active compounds.

15. The method as defined in claim 14, wherein said time interval is from 15 to 30 minutes and said temperature is from 30 to 40° C.

* * * * *